United States Patent [19]

Tang et al.

[11] Patent Number: 4,603,222
[45] Date of Patent: * Jul. 29, 1986

[54] METHOD FOR THE PREPARATION OF NITRODIPHENYL ETHERS

[75] Inventors: David Y. Tang, Amherst, N.Y.; Byron R. Cotter, Northvale, N.J.; Frederick J. Goetz, Wilmington, Del.

[73] Assignee: Occidental Chemical Corporation, Niagara Falls, N.Y.

[*] Notice: The portion of the term of this patent subsequent to Sep. 4, 2001 has been disclaimed.

[21] Appl. No.: 645,723

[22] Filed: Aug. 30, 1984

Related U.S. Application Data

[63] Continuation-in-part of Ser. No. 360,533, Mar. 22, 1982, Pat. No. 4,469,893.

[51] Int. Cl.$^4$ .............. C07C 41/16; C07C 45/64
[52] U.S. Cl. ................... 568/315; 568/424; 568/585; 568/586; 558/424; 560/21; 562/435; 564/300; 564/430
[58] Field of Search ............... 568/424, 585, 586, 315; 260/465 F; 560/21; 562/435; 564/430

[56] References Cited

U.S. PATENT DOCUMENTS 4,259,510 3/1981 Johnson .................. 568/585 X
4,469,893 9/1984 Tang et al. ................ 568/424

Primary Examiner—Bernard Helfin
Attorney, Agent, or Firm—James F. Tao; Arthur S. Cookfair

[57] ABSTRACT

Diphenyl ethers of the formula

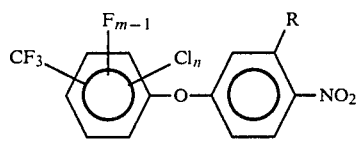

wherein m is 1–3, n is 1 or 2, R is hydrogen, carboxy, carboxylate salt or ester, formyl oxime, cyano, alkyl, alkoxy, chloro, bromo, or N, N-dialkyl amino, are prepared by reacting a chloro-fluoro-benzotrifluoride of the formula

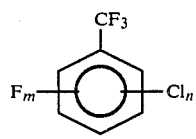

wherein m and n are as defined above with a nitrophenoxide of the formula

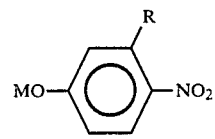

where R is defined above, and M is a cation of an alkali metal or an alkaline earth metal.

20 Claims, No Drawings

METHOD FOR THE PREPARATION OF NITRODIPHENYL ETHERS

This application is a continuation-in-part of application Ser. No. 360,533 filed Mar. 22, 1982, and now U.S. Pat. No. 4,469,843.

BACKGROUND OF THE INVENTION

This invention relates to a process for preparing trifluoromethyl-nitrodiphenyl ethers having the formula

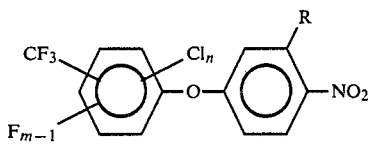

wherein m in 1 to 3, n is 1 or 2 and R is hydrogen, carboxyl, carboxylate, formyl, keto, oxime, cyano, alkyl, alkoxy, chloro, bromo, or N, N-dialkylamino. The trifluoromethylphenyl-nitrophenylethers that may be prepared by the process of this invention are members of a class of compounds useful as herbicides and/or as intermediates for the preparation of various herbicides, pesticides, dyestuffs, and pharmaceuticals. In recent years, the development of commercial utility for trifluoromethylphenyl-nitrophenylethers in the agricultural and pharmaceutical fields has led to considerable activity in the investigation of methods of preparation. The following U.S. patents disclose the preparation and/or use of various trifluoromethylphenyl-nitrophenylethers: U.S. Pat. Nos. 4,262,152; 4,031,131; 4,259,510; 3,941,830; 3,798,276; 3,928,416; 3,784,635; 4,063,929; 4,087,272; 4,263,277; 4,263,041; 4,002,662; 4,001,005; and 3,979,437.

Various methods for the preparation of 2-chloro-4-trifluoromethyl-4¹-nitrodiphenyl ethers are known. One method, disclosed in U.S. Pat. No. 4,259,510 comprises reacting a 2-chloro-4-trifluoromethylphenolate with a p-nitro-halobenzene. However, the phenolate reactant is not readily available commercially and, as a result, this synthesis route involves a preliminary step to prepare the phenolate. In another method, suggested in U.S. Pat. No. 4,031,131, a 3-chloro-4-halobenzotrifluoride is reacted with a phenoxide and the resultant diphenyl ether is subsequently nitrated. In addition to requiring an additional step, the subsequent nitration is inefficient and results in the production of undesired isomers. To avoid the disadvantage of a subsequent nitration step, the 3-chloro-4-halobenzotrifluoride may be reacted with a p-nitrophenoxide. However, it has been found that the presence of the nitro group drastically reduces the nucleophilicity of the phenoxide oxygen that is the reactive site, so that reaction with compounds such as 3,4-dichlorobenzotrifluoride are found to be extremely inefficient.

Nevertheless, it has now been found that, despite the adverse effect of the nitro group on the nucleophilicity of the phenoxide oxygen when the chlorohalobenzotrifluoride reactant is a chloro-fluorobenzotrifluoride such as 3-chloro-4-fluorobenzotrifluoride, the reaction with nitrophenoxides, especially p-nitrophenoxides can be easily affected, since the reaction of the phenoxide oxygen at the fluorine site proceeds smoothly even without a catalyst to provide the trifluoromethylphenyl-nitrophenylether product in high yield. In this matter, the need for a subsequent nitration step is eliminated. Furthermore, the method of this invention, utilizing chlorofluorobenzotrifluoride reactants is particularly suitable for reactions with nitrophenoxides carrying highly sensitive functional groups, such as aldehydes which might otherwise be further oxidized in a subsequent nitration step such as required by the prior art process described above.

Chloro-fluorobenzotrifluorides may be prepared by the vapor phase chloro-denitration reaction of the corresponding chloro-nitrobenzotrifluoride with a chlorinating agent. Thus, for example, 3-chloro-4-fluorobenzotrifluoride may be prepared by vapor phase chlorodenitration reaction of chlorine with 4-fluoro-3-nitrobenzotrifluoride. The chloro-denitration process is carried out under conditions of temperature and pressure appropriate for a vapor phase reaction, the exact conditions being dependent on the properties of the particular reactants employed. Typically, the process is carried out at atmospheric conditions and at a temperature in the range of about 250° to about 450° Celsius, preferably 300° to 400° C. Typical of the chloro-substituted benzotrifluorides that may be prepared in this manner and employed as reactants in the process of the present invention are 3-chloro-4-fluorobenzotrifluoride; 4-chloro-3-fluorobenzotrifluoride; 2-chloro-5-fluorobenzotrifluoride; 5-chloro-2-fluorobenzotrifluoride; 2-chloro-4-fluorobenzotrifluoride; 4-chloro-2-fluorobenzotrifluoride; 3-chloro-5-fluorobenzotrifluoride; 2,5-dichloro-4-fluorobenzotrifluoride; 4,5-dichloro-2-fluorobenzotrifluoride; 3,5-dichloro-4-fluorobenzotrifluoride; 3,4-difluoro-5-chlorobenzotrifluoride; 2,5-difluoro-3-chlorobenzotrifluoride; 3,5-difluoro-4-chlorobenzotrifluoride; and the like.

SUMMARY OF THE INVENTION

In accordance with the invention, trifluoromethylphenyl-nitrophenyl ethers of the formula

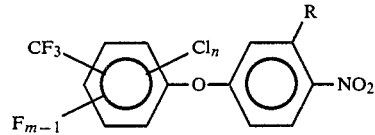

wherein m is 1 to 3, n is 1 or 2 and R is hydrogen; formyl; keto of the formula —COR' wherein R' is alkyl, preferably of 1 to 6 carbon atoms; oxime of the formula —CR"NOR''' where R" and R" are independently hydrogen or alkyl, preferably of 1 to 6 carbon atoms; cyano; alkyl, preferably 1 to 6 carbon atoms; alkoxy, preferably 1 to 6 carbon atoms; chloro; bromo; N,N-dialkylamino, the alkyl groups being preferably 1 to 4 carbon atoms, carboxyl, carboxylate salts or carboxylate esters of the formula —CO₂R wherein R² is alkyl, preferably of 1 to 6 carbon atoms are prepared by reacting a chloro-fluoro-benzotrifluoride of the formula

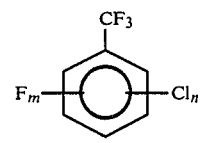

wherein m and n are defined above and m plus n is equal to or less than 4, with a nitro-phenoxide of the formula

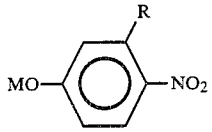

where R is defined above, and M is a cation of an alkali metal or alkaline earth metal, with the proviso that when m is 1, R is keto or oxime.

Typical chloro-fluorobenzotrifluoride reactants that may be employed in the process of this invention are 2-chloro-5-fluorobenzotrifluoride; 5-chloro-2-fluorobenzotrifluoride; 2-chloro-4-fluorobenzotrifluoride; 4-chloro-2-fluorobenzotrifluoride; 3-chloro-5-fluorobenzotrifluoride; 3-chloro-4-fluorobenzotrifluoride; 4-chloro-3-fluorobenzotrifluoride; 2,5-dichloro-4-fluorobenzotrifluoride 4,5-dichloro-2-fluorobenzotrifluoride; 3,5-dichloro-4-fluorobenzotrifluoride; 3,4-difluoro-5-chlorobenzotrifluoride; 2,5-difluoro-3-chlorobenzotrifluoride; 3,5-difluoro-4-chlorobenzotrifluoride, and the like.

The nitrophenoxide may be employed as shown as a previously prepared reactant or may be prepared in situ in the reaction mixture from the corresponding nitrophenol and an alkaline earth metal hydroxide or carbonate or, preferably an alkali metal hydroxide or carbonate. The preferred nitrophenoxides are the sodium or potassium salts. When a nitrophenol bearing a carboxylic group is employed as a reactant it is preferred to employ the di-salt of an alkali or alkaline earth metal.

Typical nitrophenoxide reactants that may be employed in the process of this invention include for example, potassium-4-nitrophenoxide; dipotassium-5-hydroxy-2-nitrobenzoic acid; sodium 3-chloro-4-nitrophenoxide; sodium-3-methyl-4-nitrophenoxide; sodium-5-hydroxy-2-nitrobenzaldehyde; potassium-3-chloro-4-nitrophenoxide; sodium 3-bromo-4-nitrophenoxide; potassium-3-ethyl-4-nitrophenoxide; and the like.

The reaction is preferably carried out in the presence of a dipolar aprotic solvent. Suitable solvents include, for example, dimethylsulfoxide, sulfolane, N-methyl-2-pyrrolidone, N, N-dimethylformamide, and the like. The reaction may be run neat utilizing the chloro-fluorobenzotrifluoride reactant as the liquid reaction medium in the presence of a phase transfer catalyst, such as a quaternary ammonium salt, a quaternary phosphonium halide or a crown ether catalyst.

The temperature at which the reaction is carried out may vary considerably but is preferably maintained in the range of about 50° to about 300° Celsius, and most preferably, in the range of about 100° to about 200° Celsius. The process is preferably carried out at atmospheric pressure. However, autogenous pressure may be employed if desired, to allow the use of higher temperatures.

The following specific examples are provided to further illustrate this invention and the manner in which it may be carried out. It will be understood, however, that the specific details given in the examples have been chosen for purpose of illustration and are not to be construed as a limitation on the invention. In the examples, unless otherwise indicated, all parts and percentages are by weight and all temperatures are in degrees Celsius.

EXAMPLE 1

In a continuous process, about 8 parts per hour of 4-fluoro-3-nitrobenzotrifluoride vapors and about 15 parts per hour of chlorine gas were passed simultaneously through a vapor phase reactor maintained at a temperature of about 320° C. and the reaction product vapors were condensed and collected. The process was continued until about 40 parts of 4-fluoro-3-nitrobenzotrifluoride had been passed through the reactor, yielding about 36.3 parts of 3-chloro-4-fluoro benzotrifluoride product. The structure of the product was confirmed by spectral analysis.

EXAMPLE 2A

About 500 parts of aqueous nitric acid was added slowly, with stirring, to a reaction vessel containing about 400 parts of 3-chloro-4-fluorobenzotrifluoride. The temperature of the reaction mixture was maintained at about 40° C. during the addition, then raised to about 60° C. and maintained thereat for about 5 hours. The reaction mixture was allowed to settle. The aqueous layer was removed and the organic layer was washed twice with 500 parts of water, treated several times with a saturated solution of sodium bicarbonate, washed with water again, dried over anhydrous magnesium sulfate, and filtered. The filtrate was distilled at reduced pressure to yield 347 parts of 5-chloro-4-fluoro-2-nitrobenzotrifluoride.

EXAMPLE 2B

In a continuous process, about 14 parts per hour of 5-chloro-4-fluoro-2-nitrobenzotrifluoride vapors and about 12 parts per hour of chlorine gas were passed simultaneously through a vapor phase reactor maintained at a temperature of about 320° to 380° C. The vaporized reaction product was condensed and collected. The process was continued until about 14.7 parts of 5-chloro-4-fluoro-2-nitrobenzotrifluoride had been added and 14.7 parts of 2,5-dichloro-4-fluorobenzotrifluoride product was collected. The structure of the product was confirmed by gas chromatography—mass spectrum, $F^{19}$ and $C^{13}$ nuclear magnetic resonance analysis.

EXAMPLE 3

In a continuous process, about 14 parts per hour of 2-fluoro-5-nitrobenzotrifluoride vapors and about 12 parts per hour of chlorine gas were passed simultaneously through a vapor phase reactor maintained at a temperature of about 320° to 380° C. The vaporized reaction product was condensed and collected. The process was continued until about 20 parts of 2-fluoro-5-nitrobenzotrifluoride and about 17.3 parts of chlorine gas had been passed through the reactor. Analysis of the reaction product indicated 16.7 parts of 5-chloro-2-fluorobenzotrifluoride, a yield of 89%. The structure of the product was confirmed by gas chromatography—mass spectrum $F^{19}$ and $C^{13}$ nuclear magnetic resonance analysis.

EXAMPLE 4

14.1 parts of 5-fluoro-2-nitrobenzotrifluoride vapors and 12.1 parts of chlorine gas were passed simultaneously, over a one-hour period, through a vapor-phase reactor maintained at a temperature of about 320° to 380° C. The vaporized reaction product was condensed and collected. Analysis of the reaction product indicated 12.6 parts of 2-chloro-5-fluorobenzotrifluoride, a yield of 94%. The structure of the product was confirmed by gas chromatography—mass spectrum $F^{19}$ and $C^{13}$ nuclear magnetic resonance analysis.

EXAMPLE 5

A mixture of 2.66 parts of potassium 4-nitrophenoxide; 3.9 parts of 3-chloro-4-fluorobenzotrifluoride and 126 parts of sulfolane was heated to about 142° C. and maintained thereat, with stirring for about 2 hours, then cooled to about room temperature, diluted with water and extracted with diethylether. The ether layer was dried and the ether removed under reduced pressure to yield 6.2 parts of a crude product. Gas chromatographic-mass spectrum analysis confirmed the major product as 4-(2-chloro-4-trifluoromethylphenoxy)-nitrobenzene.

EXAMPLE 6

A mixture of 2 parts of potassium 4-nitrophenoxide; 2.3 parts of 3-chloro-4-fluorobenzotrifluoride and 26 parts of N-methylpyrrolidone, was sealed in a pressure vessel and heated to about 160° C. The reaction mixture was maintained at that temperature, under autogenous pressure, with vigorous stirring for about 3 hours, then cooled to about room temperature diluted with water and extracted with diethyl ether. The ether layer was dried and concentrated. Analysis of the reaction product, by gas chromatographic-mass spectrum confirmed the major product to be 4-(2-chloro-4-trifluoromethylphenoxy)-nitrobenzene.

EXAMPLE 7

The process of Example 6 is repeated except that in place of 3-chloro-4-fluorobenzotrifluoride, there is substituted an equal amount of 2-chloro-5-fluorobenzotrifluoride, and the product prepared is 4-(4-chloro-3-trifluoro-methylphenoxy)-nitrobenzene.

EXAMPLE 8

The process of Example 6 is repeated except that in place of 3-chloro-4-fluorobenzotrifluoride there is substituted an equal amount of 5-chloro-2-fluorobenzotrifluoride and the product prepared is 4-(4-chloro-2-trifluoromethylphenoxy)-nitrobenzene.

EXAMPLE 9

The process of Example 6 is repeated except that in place of 3-chloro-4-fluorobenzotrifluoride, there is substituted an equimolar amount of 2,5-dichloro-4-fluorobenzotrifluoride and the product prepared is 4-(2,5-dichloro-4-trifluoromethylphenoxy)-nitrobenzene.

EXAMPLE 10

To a solution of 10 parts of 5-hydroxy-2-nitrobenzoic acid in 320 parts of methanol, was added 6.1 parts of potassium hydroxide. The mixture was allowed to react under ambient conditions for about one hour. The resulting dipotassium salt of 5-hydroxy-2-nitrobenzoic acid was dried by removing the solvent under reduced pressure. The dipotassium salt was then combined with 380 parts of sulfolane; 310 parts of N-methyl-2-pyrrolidone; and 50 parts of 3-chloro-4-fluorobenzotrifluoride. The mixture was heated to about 150° C. and maintained thereat for about 24 hours, then cooled, acidified with hydrochloric acid and extracted with diethyl ether. The ether extract was washed with water and dried over anhydrous magnesium sulfate. The ether and the excess 3-chloro-4-fluorobenzotrifluoride were removed under vacuum to yield a crude yellow-brown product. Mass spectrographic analysis indicated 5-(2-chloro-4-trifluoromethlyphenoxy)-2-nitrobenzoic acid as a major component.

EXAMPLE 11

A mixture of 16.7 parts of 5-hydroxy-2-nitrobenzaldehyde and 6.6 parts of potassium hydroxide in about 120 parts of methanol was stirred at room temperature for about one hour. The solvent was then evaporated at reduced pressure to recover the potassium salt of the phenolates as a dry solid. To this was added 30 parts of 3-chloro-4-fluorobenzotrifluoride and about 154 parts of N-methyl-2-pyrrolidone. The mixture was stirred at 140°–150° C. for about one hour, then cooled, diluted with water, acidified with 10% hydrochloric acid, and extracted several times with diethyl ether. The ether layer was washed with a 10% aqueous potassium hydroxide solution. Then with water, and dried over anhydrous magnesium sulfate. The dried ether solution was then concentrated by evaporation under reduced pressure to yield 5-(2-chloro-4-trifluoromethylphenoxy)-2-nitrobenzaldehyde as the major product. The structure of 5-(2-chloro-4-trifluoromethylphenoxy)-2-nitrobenzaldehyde was confirmed by gas chromatography—mass spectrum analysis.

EXAMPLE 12

(A) A mixture of 20 parts of m-hydroxy-acetophenone and 60 parts of methylene chloride was cooled to 0°–5° C. and maintained thereat, with stirring, while 26.9 parts of mixed acid (20% oleum and 90% HNO$_3$) was added slowly. The mixture was stirred for an additional 30 minutes then poured on crushed ice. The organic layer was separated from the aqueous layer and the aqueous layer was extracted with additional methylene chloride. The organic product was dried and concentrated to afford a viscous brown. Spectral analysis indicated the major products to be 3-hydroxy-6-nitroacetophenone (I) and 3-hydroxy-4-nitroacetophenone (II) in a ratio (I:II) of 57:43.

(B) A mixture of 5.17 parts of mixed mono-nitrated hydroxyacetophenone (prepared as detailed in part A, above) and 1.3 parts of sodium hydroxide in 20 parts of dimethyl sulfoxide was stirred at room temperature for one hour. 3-Chloro-4-fluorobenzotrifluoride (6.24 parts) was added. The mixture was heated to 140°–150° C. and maintained thereat, with stirring, for about 4.5 hours, then cooled to room temperature and poured into water. The aqueous mixture was extracted twice with diethyl ether and the organic extracts combined, dried and concentrated. Spectral analysis indicated 5-(2-chloro-4-trifluoromethylphenoxy)-2-nitro-acetophenone as a major product.

EXAMPLE 13

A mixture of 0.43 parts of mononitrated hydroxyacetophenone (prepared as in Example 12A, above) and 0.1 part of sodium hydroxide, in 5.0 parts of dimethylsulfoxide was stirred for one hour at room temperature. To the mixture, 0.43 parts of 3-chloro-4-,5-difluorobenzotrifluoride was added. The mixture was heated to about 140°–150° C. and maintained thereat for about 4 hours, then cooled to room temperature, poured into water, extracted twice with diethyl ether and the organic extracts combined, dried and concentrated. Analysis using gas chromatography-mass spectrometry indicated 5(2-chloro-6-fluoro-4-trifluoromethylphenoxy)-2-nitroacetophenone to be a major product.

EXAMPLE 14

A mixture of 0.33 parts of 3-hydroxy-6-nitrobenzaldehyde and 0.1 part of sodium hydroxide in 5 parts of dimethylsulfoxide was stirred for one hour at room temperature. To the mixture was added 0.43 part of 3-chloro-4,5-difluorobenzotrifluoride. The mixture was heated to 140°–150° C. and maintained thereat, with stirring, for 4 hours, then cooled to room temperature and poured into water. The aqueous mixture was extracted twice with diethyl ether and the organic extracts combined, dried and concentrated. Analysis of the producing using gas chromatography-mass spectrometry indicated 5-(2-chloro-6-fluoro-4-trifluoromethylphenoxy)-2-nitrobenzaldehyde to be a major component.

What is claimed is:

1. A process for the preparation of diphenyl ethers of the formula

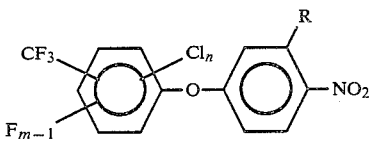

wherein m is 1 to 3, n is 1 to 2, R is hydrogen; formyl; keto of the formula —COR' wherein R' is alkyl; cyano; alkyl, of 1 to 6 carbon atoms; alkoxy, of 1 to 6 carbon atoms; chloro; bromo; N, N-dialkyl amino, the alkyl group being preferably 1 to 4 carbon atoms; carboxyl, carboxylate salts; or carboxylate esters of the formula $CO_2R'$ wherein R' is alkyl of 1 to 6 carbon atoms, which comprises reacting a chlorofluorobenzotrifluoride of the formula

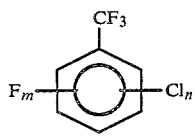

where m and n are as defined above m plus n is equal to or less than 4, with a nitro-phenoxide of the formula

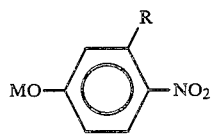

where R is defined above, and M is a cation of alkali metal or an alkaline earth metal, with the proviso that when m is 1 R is keto.

2. A process according to claim 1 for the preparation of a diphenyl ether of the formula

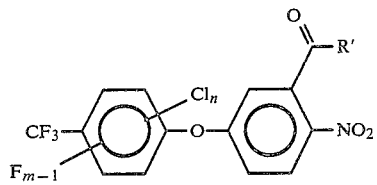

where m is 1 to 3, n is 1 to 2, and R' is alkyl of 1 to 6 carbon atoms, which comprises reacting a chlorofluorobenzotrifluoride of the formula

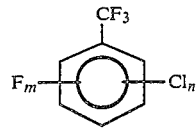

where m and n are as defined above and m plus n is equal to or less than 3, with a nitrophenoxide of the formula

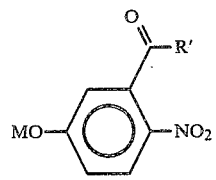

where R' is defined above and M is a cation of an alkali metal or an alkaline earth metal.

3. A process according to claim 2 wherein m is 1 and n is 1.

4. A process according to claim 2 wherein m is 2 and n is 1.

5. A process according to claim 2 wherein m is 1 and n is 2.

6. A process according to claim 2 wherein the chlorofluorobenzotrifluoride is 2-chloro-5-fluorobenzotrifluoride.

7. A process according to claim 2 wherein the chlorofluorobenzotrifluoride is 5-chloro-2-fluorobenzotrifluoride.

8. A process according to claim 2 wherein the chlorofluorobenzotrifluoride is 2,5-dichloro-4-fluorobenzotrifluoride.

9. A process according to claim 2 wherein the chlorofluorobenzotrifluoride is 3-chloro-4-fluorobenzotrifluoride.

10. A process according to claim 2 wherein the chloro-fluorobenzotrifluoride is 3,5-dichloro-4-fluorobenzotrifluoride.

11. A process according to claim 1 wherein the chloro-fluorobenzotrifluoride is 3-chlor-4,5-difluorobenzotrifluoride.

12. A process according to claim 1 carried out in a dipolar, aprotic solvent.

13. A process according to claim 12 wherein M is a cation of an alkali metal.

14. A process according to claim 12 wherein R is hydrogen.

15. A process according to claim 12 wherein R is an alkali metal carboxylate.

16. A process according to claim 12 carried out at a temperature of about 50° to about 300° Celsius.

17. A process according to claim 16 carried out at autogenous pressure.

18. A process according to claim 16 carried out at atmospheric pressure.

19. A process according to claim 1 wherein R is keto of the formula —COR' wherein R' is an alkyl group of 1 to 6 carbon atoms.

20. A process according to claim 19 whrein R' is —CH3.

* * * * *